(12) United States Patent
Chinta et al.

(10) Patent No.: US 9,089,832 B2
(45) Date of Patent: Jul. 28, 2015

(54) CATALYSTS FOR OXIDATIVE COUPLING OF HYDROCARBONS

(75) Inventors: Sivadinarayana Chinta, Missouri City, TX (US); Joseph Thorman, Houston, TX (US); James Butler, League City, TX (US)

(73) Assignee: FINA TECHNOLOGY, INC., Houston, TX (US)

( * ) Notice: Subject to any disclaimer, the term of this patent is extended or adjusted under 35 U.S.C. 154(b) by 544 days.

(21) Appl. No.: 12/494,088

(22) Filed: Jun. 29, 2009

(65) Prior Publication Data

US 2010/0331174 A1 Dec. 30, 2010

(51) Int. Cl.
| | |
|---|---|
| B01J 23/00 | (2006.01) |
| B01J 23/10 | (2006.01) |
| B01J 23/02 | (2006.01) |
| B01J 23/06 | (2006.01) |
| B01J 23/04 | (2006.01) |
| B01J 23/36 | (2006.01) |
| C07C 2/84 | (2006.01) |

(52) U.S. Cl.
CPC ............ *B01J 23/04* (2013.01); *B01J 23/002* (2013.01); *B01J 23/10* (2013.01); *B01J 23/36* (2013.01); *C07C 2/84* (2013.01); *B01J 2523/00* (2013.01); *C07C 2521/10* (2013.01); *C07C 2523/02* (2013.01); *C07C 2523/04* (2013.01); *C07C 2523/10* (2013.01); *C07C 2523/36* (2013.01)

(58) Field of Classification Search
USPC ............................................. 502/303; 11/303
See application file for complete search history.

(56) References Cited

U.S. PATENT DOCUMENTS

| | | | |
|---|---|---|---|
| 4,239,658 A | 12/1980 | Mitchell, III et al. | |
| 4,450,310 A * | 5/1984 | Fox et al. | 585/400 |
| 4,499,324 A * | 2/1985 | Gaffney | 585/500 |
| 4,523,049 A * | 6/1985 | Jones et al. | 585/500 |
| 4,656,144 A | 4/1987 | Hosaka et al. | |
| 4,658,076 A | 4/1987 | Kolts et al. | |
| 4,658,077 A | 4/1987 | Kolts et al. | |
| 4,672,145 A | 6/1987 | Kolts et al. | |
| 4,704,487 A | 11/1987 | Devries et al. | |
| 4,704,493 A | 11/1987 | Devries et al. | |
| 4,774,216 A | 9/1988 | Kolts et al. | |
| 4,775,654 A | 10/1988 | Kolts et al. | |
| 4,780,449 A * | 10/1988 | Hicks | 502/303 |
| 4,826,796 A | 5/1989 | Erekson et al. | |
| 4,895,823 A | 1/1990 | Kolts et al. | |
| 4,950,827 A | 8/1990 | Erekson et al. | |
| 4,950,830 A | 8/1990 | Erekson et al. | |
| 4,950,836 A | 8/1990 | Kimble et al. | |
| 4,956,327 A | 9/1990 | Erekson et al. | |
| 4,962,252 A | 10/1990 | Wade | |
| 4,982,038 A | 1/1991 | Kimble et al. | |
| 5,081,324 A * | 1/1992 | Michaels et al. | 585/500 |
| 5,087,787 A | 2/1992 | Kimble et al. | |
| 5,097,086 A | 3/1992 | Lee et al. | |
| 5,105,045 A | 4/1992 | Kimble et al. | |
| 5,118,899 A | 6/1992 | Kimble et al. | |
| 5,132,482 A | 7/1992 | Smith et al. | |
| 5,146,027 A | 9/1992 | Gaffney | |
| 5,157,188 A | 10/1992 | Kolts et al. | |
| 5,160,502 A | 11/1992 | Kimble et al. | |
| 5,210,357 A | 5/1993 | Kolts et al. | |
| 5,238,898 A * | 8/1993 | Han et al. | 502/324 |
| 5,406,017 A | 4/1995 | Withers, Jr. | |
| 5,527,978 A * | 6/1996 | Fornasari et al. | 585/500 |
| RE35,632 E * | 10/1997 | Leyshon | 585/500 |
| 5,712,217 A * | 1/1998 | Choudhary et al. | 502/303 |
| 5,959,170 A | 9/1999 | Withers, Jr. | |
| 6,020,533 A | 2/2000 | Lewis et al. | |
| 6,096,934 A | 8/2000 | Rekoske | |
| 2002/0173420 A1 | 11/2002 | Cantrell et al. | |
| 2007/0055083 A1 | 3/2007 | Bagherzadeh et al. | |
| 2008/0281136 A1 | 11/2008 | Bagherzadeh et al. | |
| 2009/0293359 A1* | 12/2009 | Simmons et al. | 48/127.7 |

OTHER PUBLICATIONS

Bukur, Dragomir; Promoter Effects on Precipitated Iron Catalysts for Fischer Tropsch Synthesis, 1990, American Chemical Society, vol. 29, p. 194-204.*
Haber, Block and Delmon. "Manual of Methods and Procedures for Catalyst Characterization", Pure & Appl. Chem., vol. 67, Nos. 8/9, pp. 1257-1306 (1995).
Khan and Ruckenstein. "Oxidative Methylation of Toluene with Methane over Superbasic Catalysts: A Selective Route to Styrene and Ethylbenzene through Alternative Feedstocks", Journal of Catalysis 143, pp. 1-21 (1993).
Lunsford, J.H. "The Catalytic Oxidative Coupling of Methane", Angew, Chem. Intl. Ed. Engl. 34, p. 970 (1995).

* cited by examiner

*Primary Examiner* — Melvin C Mayes
*Assistant Examiner* — Michael Forrest

(57) ABSTRACT

A catalyst includes: (A) at least one element selected from the group consisting of the Lanthanoid group, Mg, Ca, and the elements of Group 4 of the periodic table (Ti, Zr, and Hf); (B) at least one element selected from the group consisting of the Group 1 elements of Li, Na, K, Rb, Cs, and the elements of Group 3 (including La and Ac) and Groups 5-15 of the periodic table; (C) at least one element selected from the group consisting of the Group 1 elements of Li, Na, K, Rb, Cs, and the elements Ca, Sr, and Ba; and (D) oxygen.

18 Claims, 6 Drawing Sheets

CATALYSTS FOR OXIDATIVE COUPLING OF HYDROCARBONS

CROSS-REFERENCE TO RELATED APPLICATIONS

The present invention is related to co-pending applications titled: Process For The Oxidative Coupling Of Methane; and Process For The Oxidative Coupling Of Hydrocarbons, both filed by Fina Technology, Inc. on the same date as the present application.

FIELD

The present invention generally relates to catalysts that can be used in hydrocarbon reactions.

BACKGROUND

Methane is a primary component of natural gas. Although natural gas can be useful as a fuel, natural gas sources can be remote, and often, it is not cost effective to transport the methane. One method of transporting natural gas is by liquefying the gas, however, the boiling point of methane is low enough that liquefaction can be difficult and expensive. Research has been conducted to find new and cost-effective ways of utilizing this resource.

One possible solution is to convert methane to higher hydrocarbons such as ethane or ethylene. Ethylene and higher hydrocarbons can be more easily liquefied and transported from remote sites and can also be valuable products. Ethylene, for one, can be a valuable product, as it can be used for the production of styrene, and has many other uses, such as the production of polyethylene, ethanol, ethylene glycol, and polyvinyl chloride.

Traditionally, ethylene is obtained predominantly from the thermal cracking of hydrocarbons, such as ethane, propane, butane, or naphtha. Ethylene can also be produced and recovered from various refinery processes. Ethylene from these sources can also include a variety of undesired products, including diolefins and acetylene, which can be costly to separate from the ethylene. Separation methods can include, for example, extractive distillation and selective hydrogenation of the acetylene back to ethylene. Thermal cracking and separation technologies for the production of relatively pure ethylene can result in significant production costs. Thus, the production of ethylene from methane rather than by some of the traditional routes could decrease ethylene production costs.

SUMMARY

An embodiment of the present invention is a catalyst that includes (A) at least one element selected from the group consisting of the Lanthanoid group, Mg, Ca, and the elements of Group 4 of the periodic table (Ti, Zr, and Hf). The catalyst further includes (B) at least one element selected from the group consisting of the Group 1 elements of Li, Na, K, Rb, Cs, and the elements of Group 3 (including La and Ac) and Groups 5-15 of the periodic table and (C) at least one element selected from the group consisting of the Group 1 elements of Li, Na, K, Rb, Cs, and the elements Ca, Sr, and Ba; along with (D) oxygen. If an element from Group 1 of the periodic table is used in (B), it cannot be used in (C).

The element(s) selected from (A) can range from 40 to 90 wt % of the catalyst. The element(s) selected from (B) can range from 0.01 to 40 wt % of the catalyst. The element(s) selected from (C) can range from 0.01 to 40 wt % of the catalyst. The oxygen in (D) can range from 10 to 45 wt % of the catalyst.

The catalyst can be calcined by heating the catalyst to elevated temperatures, such as above 750° C.

The catalyst can be used in a reactor for the oxidative coupling of methane. For OCM, the temperature can be from 500° C. to 750° C., optionally from 600° C. to 750° C. The molar ratio of methane to oxygen can be from 1:1 to 100:1, optionally from 4:1 to 80:1.

The catalyst can also be used in a reactor for the oxidative methylation of toluene. For OMT, the temperature can be from 500° C. to 800° C., optionally from 550° C. to 700° C. The molar ratio of methane to oxygen can be from 1:1 to 100:1, optionally from 4:1 to 80:1. The molar ratio of methane to toluene can be from 1:1 to 50:1, optionally from 8:1 to 30:1.

For both the processes of OCM and OMT, as well as other coupling and cross-coupling of hydrocarbons reactions, adjustments in certain reaction conditions, such as temperature, can be used to control product selectivity. Adjusting the temperature can also alter the exotherm produced by oxidative coupling.

DETAILED DESCRIPTION

Figure 1:
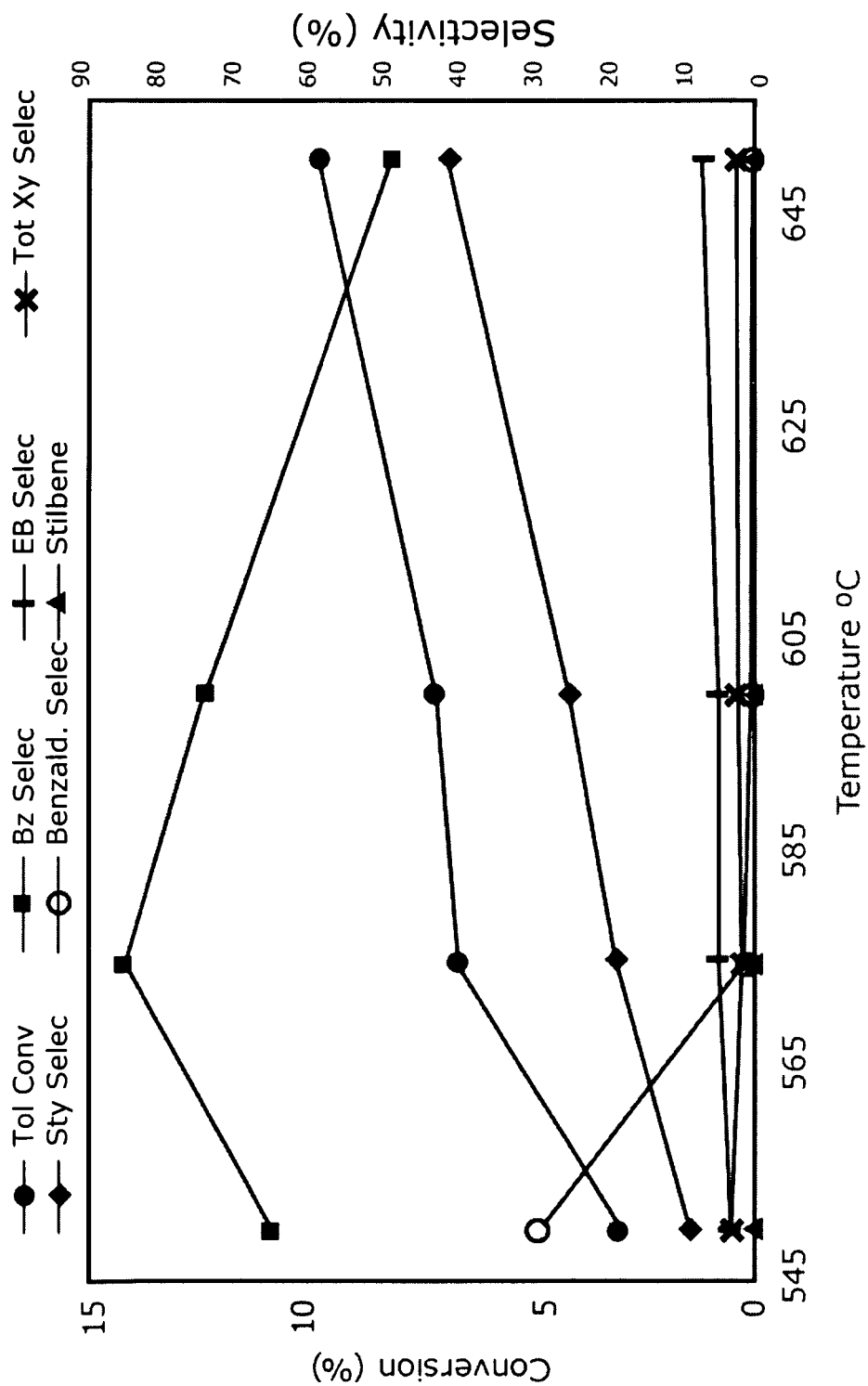
FIG. 1 is a chart showing data, including conversion and selectivity, of the OMT trial runs conducted in Comparative Example A.

The results of oxidative coupling can be influenced by many factors, such as reaction conditions, source and contents of the feed, and reactor design. The catalyst used for the reaction can be one of the most important factors. The effectiveness of the reaction can be measured in terms of conversion, selectivity, and yield. Conversion refers to the percentage of reactant (e.g. methane, toluene) that undergoes a chemical reaction. Selectivity refers to the relative activity of a catalyst in reference to a particular compound in a mixture. Selectivity is quantified as the proportion of a particular product relative to all others.

A catalyst comprising a substrate that supports a metal or a combination of metals can be used to catalyze the reaction of hydrocarbons, such as in the oxidative coupling of methane (OCM) or cross-coupling of hydrocarbons, such as the oxidative methylation of toluene (OMT). The method of preparing the catalyst, pretreatment of the catalyst, and reaction conditions can influence the conversion, selectivity, and yield of OCM, OMT, and similar processes.

According to one embodiment, the catalyst of the present invention can include a substrate, one or more metal promoters and oxygen. According to an embodiment, the catalyst of the present invention can include a substrate that ranges from 40 to 90 wt % of the catalyst, the substrate made of one or more of the elements of Set A consisting of: the Lanthanoid group (La, Ce, Pr, Nd, Sm, Eu, Gd, Tb, Dy, Ho, Er, Th, Yb, Lu), Mg, Ca, and the elements of Group 4 of the periodic table (Ti, Zr, and Hf). The substrate supports a first promoter that ranges from 0.01 to 40 wt % of the catalyst chosen from one or more of the elements of Set B consisting of: Li, Na, K, Rb, Cs, and the elements of Group 3 (including La and Ac) and Groups 5-15 of the periodic table. The substrate further supports a second promoter that ranges from 0.01 to 40 wt % of the catalyst chosen from one or more of the elements of Set C consisting of: Li, Na, K, Rb, Cs, Ca, Sr, and Ba. If an element from Group 1 of the periodic table (Li, Na, K, Rb, Cs) is used as a catalytic element from Set B it cannot be used as a catalytic element from Set C. The catalyst further includes Set D, which consists of oxygen, in a range of 10 to 45 wt %. All percentages are for the catalyst after calcination.

The catalyst contains at least one element from each of the Sets A, B, C, and D in the ranges given above. At least 90 wt % of the catalyst is made of the elements of Sets A, B, C and oxygen in the final catalyst composition after a calcination procedure. Optionally at least 95 wt % of the catalyst is made of the elements of Sets A, B, C and D in the final catalyst after a calcination procedure. Residual anions may be present in the final catalyst, e.g. nitrate, halide, sulfate and acetate. The catalyst can vary in terms of its activity, its basicity, its lifetime, and other characteristics. This variation can be influenced by the selection of the elements chosen from Sets A, B, C and D and their respective content in the catalyst.

The various elements that make up the catalyst can be derived from any suitable source, such as in their elemental form, or in compounds or coordination complexes of an organic or inorganic nature, such as carbonates, oxides, hydroxides, nitrates, acetates, chlorides, phosphates, sulfides and sulfonates. The elements and/or compounds can be prepared by any suitable method, known in the art, for the preparation of such materials.

The term "substrate" as used herein is not meant to indicate that this component is necessarily inactive, while the other metals and/or promoters are the active species. On the contrary, the substrate can be an active part of the catalyst. The term "substrate" would merely imply that the substrate makes up a significant quantity, generally 40% or more by weight, of the entire catalyst. The promoters individually can range from 0.01% to 40% by weight of the catalyst, optionally from 0.01% to 10%. If more than one promoters are combined, they together generally can range from 0.01% up to 50% by weight of the catalyst. The elements of the catalyst composition can be provided from any suitable source, such as in its elemental form, as a salt, as a coordination compound, etc.

The addition of a support material to improve the catalyst physical properties is possible within the present invention. Binder material, extrusion aids or other additives can be added to the catalyst composition or the final catalyst composition can be added to a structured material that provides a support structure. For example, the final catalyst composition can be supported by a structured material comprising an alumina or aluminate framework. The content of such a binder material, extrusion aids, structured material, or other additives, and their respective calcination products, will not be taken into consideration within the stated percentage ranges of Sets A-D stated herein. As an additional example a binder material, which can contain elements that are contained within Sets A-D, can be added to the catalyst composition. Upon calcination these elements can be altered, such as through oxidation which would increase the relative content of oxygen within the final catalyst structure. The binder material elements and the calcination products are not taken into consideration within the stated percentage ranges of Sets A-D stated herein. The combination of the catalyst of the present invention combined with additional elements such as a binder, extrusion aid, structured material, or other additives, and their respective calcination products, are included within the scope of the invention.

In one aspect, the invention is a method for the preparation of an oxidative catalyst for OCM, OMT, or another oxidative coupling reaction. In one embodiment, the catalyst can be prepared by combining a substrate chosen from at least one element from Set A with at least one promoter element chosen from Set B, at least one promoter element chosen from Set C, and oxygen from Set D. The present invention is not limited by the method of catalyst preparation, and all suitable methods should be considered to fall within the scope herein. Particularly effective techniques are those utilized for the preparation of solid catalysts. Conventional methods include co-precipitation from an aqueous, an organic or a combination solution-dispersion, impregnation, dry mixing, wet mixing or the like, alone or in various combinations. In general, any method can be used which provides compositions of matter containing the prescribed components in effective amounts. According to an embodiment the substrate is charged with promoter via an incipient wetness impregnation. Other impregnation techniques such as by soaking, pore volume impregnation, or percolation can optionally be used. Alternate methods such as ion exchange, wash coat, precipitation, and gel formation can also be used. Various methods and procedures for catalyst preparation are listed in the technical report Manual of Methods and Procedures for Catalyst Characterization by J. Haber, J. H. Block and B. Dolmon, published in the International Union of Pure and Applied Chemistry, Volume 67, Nos 8/9, pp. 1257-1306, 1995, incorporated herein in its entirety.

In an embodiment, the substrate can be a metal oxide of one or more elements of Set A. One example of an oxide substrate useful for the present invention is magnesium oxide, MgO. The oxide substrate can be either obtained commercially or produced in the lab. For instance, a metal oxide can be made by thermal decomposition of its corresponding salt at elevated temperatures up to 750° C. The choice of precursor salt from which the oxide substrate is produced can have some effect on the performance of the eventual catalyst.

When slurries, precipitates or the like are prepared, they will generally be dried, usually at a temperature sufficient to volatilize the water or other carrier, such as from 100° C. to 250° C. Irrespective of how the components are combined and irrespective of the source of the components, the dried composition is generally calcined in the presence of a free oxygen-containing gas, usually at temperatures between about 300° C. and about 900° C. for from 1 to 24 hours. The calcination can be in an oxygen-containing atmosphere, or alternately in a reducing or inert atmosphere.

Depending on the catalyst, a pretreatment of the catalyst may, or may not, be necessary. In one embodiment the invention involves the pretreatment of an oxidative catalyst for OCM, OMT, or another oxidative coupling reaction. The prepared catalyst can be ground, pressed and sieved and loaded into a reactor. The reactor can be any type known in the art to make catalyst particles, such as a fixed bed, fluidized bed, or swing bed reactor. The reactor set-up can optionally include a recycle stream. Optionally an inert material, such as quartz chips, can be used to support the catalyst bed and to place the catalyst within the bed. For the pretreatment, the reactor can be heated to elevated temperatures, such as 800° C. to 900° C. with an air flow, such as 100 mL/min, and held at these conditions for a length of time, such as 1 to 3 hours.

Then, the reactor can be cooled down to a temperature of around the operating temperature of the reactor, for example 500° C. to 650° C., or optionally down to atmospheric or other desired temperature. The reactor can be kept under an inert purge, such as under helium.

In another aspect, the invention involves reaction conditions for OCM, OMT, or another oxidative coupling reaction. Several parameters including feed composition, molar ratio of hydrocarbon reactant to oxygen, temperature, pressure, time on stream, preparation method, particle size, porosity, surface area, contact time and others can influence the outcome of the reaction. For almost every reaction condition, there can be a range of values best suited to oxidative coupling. Measures are generally taken to increase conversion and selectivity.

For the oxidative coupling of methane, contents of the feed can include methane and an oxygen source. Oxygen is a required component of the feed for oxidative coupling. Methane can be obtained from natural gas, or from organic sources, such as the decomposition of waste through fermentation. Whatever the source, methane used in OMT should not contain contaminants that might significantly interfere or give a detrimental effect on the oxidative coupling reaction. The oxygen source can be any source suitable for providing oxygen to the reaction zone such as pure oxygen, oxygen-enriched air, or air. The gas containing oxygen should not contain any contaminants that might significantly interfere with the oxidative coupling reaction. Alternate sources of oxygen may also be used, such as nitrobenzene, nitrous oxide, or other oxygen containing compounds.

Although contaminants that might significantly interfere with the oxidative coupling reaction should be avoided, the addition of trace quantities of a reaction modulator may be useful. Reaction modulators can be used for the control or alteration of conversion, selectivity, or activity of a particular catalyst or in response to certain reaction conditions. Non-limiting examples of possible reaction modulators include chlorine, ethylene and carbon monoxide.

Inert diluents such as helium and nitrogen may be included in the feed to adjust the gas partial pressures. Optionally, $CO_2$ or water (steam) can be included in the feed stream as these components may have beneficial properties, such as in the prevention of coke deposits. The pressure for oxidative coupling reactions can generally range from 1 psia to 200 psia or more. The reaction pressure is not a limiting factor regarding the present invention and any suitable condition is considered to be within the scope of the invention.

The temperature for oxidative coupling reactions can generally range from 500° C. to 800° C., optionally from 600° C. to 750° C. The reaction temperature is not a limiting factor regarding the present invention and any suitable condition is considered to be within the scope of the invention. The methane to oxygen molar ratio can range from 1:1 to 100:1, optionally from 4:1 to 80:1.

Any suitable space velocity can be considered to be within the scope of the invention. As used herein the space velocity shall be defined as: space velocity=[feed flow as vapor ($cm^3$/h)]/[catalyst weight (g)]. A standard reference temperature and pressure (72° F. and 14.7 psia) is used to convert a liquid under these conditions, such as toluene, to a feed vapor flow. For example: 0.076 $cm^3$/min of liquid toluene is converted into moles and then using 22.4 L/mol (as if it were an ideal gas) it is converted into a vapor flow of 16 $cm^3$/min. The space velocity can generally range from 15,000 $cm^3$ $g^{-1}$ $h^{-1}$ to 100,000 $cm^3$ $g^{-1}$ $h^{-1}$, optionally from 20,000 $cm^3$ $g^{-1}$ $h^{-1}$ to 85,000 $cm^3$ $g^{-1}$ $h^{-1}$. This range is an indication of possible space velocities, such as for a fixed bed reactor. Of course altering the catalyst composition, the amount of inert material, etc can alter the space velocity outside of this range. Also a change in the reactor from a fixed bed to an alternate design, such as a fluidized bed can also dramatically change the relative space velocity and can be outside of the stated range above. The space velocity ranges given are not limiting on the present invention and any suitable condition is considered to be within the scope of the invention.

For the oxidative methylation of toluene, as well as other cross-coupling reactions involving hydrocarbons, the reaction conditions can be similar to those described for the oxidative coupling of methane. The contents of the feed, of course, will be different. In the case of OMT, the feed will include toluene along with methane and oxygen. The toluene can be vaporized and introduced to the reactor either by passing the oxygen and methane gas mixture through a toluene vapor saturator right before the inlet of the reactor tube, or by syringe-pumping the liquid toluene into the gas flow and vaporizing it in a preheated zone (250~300° C.) before entering the reactor. The methane to oxygen molar ratio can be from 1:1 to 100:1, optionally from 4:1 to 80:1. The molar ratio of methane to toluene can be from 1:1 to 50:1, optionally from 8:1 to 30:1. Temperature can be from 300° C. to 900° C., optionally from 350° C. to 750° C.

The following equations, Equations 1-2, are reactions that can take place in the reactor over the OCM catalyst. The equations are shown along with their change in enthalpy, or heat of reaction. As Equations 1-2 demonstrates the reactions that occur during OCM are exothermic.

$$2CH_4 + 0.5O_2 \rightarrow C_2H_6 + H_2O; \Delta H = -174.2 \text{ kJ/mole} \qquad \text{Equation 1.}$$

$$C_2H_6 + 0.5O_2 \rightarrow C_2H_4 + H_2O; \Delta H = -103.9 \text{ kJ/mole} \qquad \text{Equation 2.}$$

The following examples are intended to give a better understanding of certain aspects and embodiments of the present invention and are not intended to limit the scope of the invention in any way.

COMPARATIVE EXAMPLE A

An oxidative catalyst was prepared comprising a MgO substrate that was promoted with Ba. The Ba/MgO catalyst was used in the oxidative coupling of methane and the oxidative methylation of toluene. The catalyst included 5% Ba by weight and was prepared from barium nitrate (6.53 g) (Sigma Aldrich, 98.0%) and MgO (23.46 g) (Fisher, 99%) by incipient wetness impregnation methodology in aqueous solution. The mixture was dried at 120° C. for 3 h and then calcined at 850° C. in air for 1 h. The catalyst was ground, pressed and sieved to 20-40 mesh size (420-841 μm) and 0.577 g of catalyst was loaded into a quartz reactor using quartz wool plugs and quartz chips to hold the catalyst bed in place. For catalyst pretreatment, the reactor was heated to 850° C. under 100 ml/min of air and held for 2 hours. The reactor was then cooled down to 600° C. under helium to prepare for the OCM and OMT experiments.

Two OCM trials were conducted. In one trial, the reactor temperature was 600° C.; in the other trial, the reactor temperature was 650° C. All reaction conditions other than temperature were held constant during the two trials. The oxygen source was air. The methane to oxygen molar ratio was 5:1. The total flow of gasses was 500 $cm^3$/min (250 $cm^3$/min air and 250 $cm^3$/min methane), and space velocity of 51,993 $cm^3$ $g^{-1}$ $h^{-1}$. The following table shows the results of the two trials. $C_2$ selectivity as used herein is the cumulative selectivity of acetylene, ethane, and ethylene.

TABLE 1

Results for OCM over Ba/MgO catalyst

| | Reaction Temperature | |
|---|---|---|
| | 600° C. | 650° C. |
| Methane Conversion (mol %) | 0.3 | 14.3 |
| $C_2$s selectivity (%) | 54.3 | 68.2 |
| Acetylene Selectivity (%) | 0 | 5.3 |
| Ethane Selectivity (%) | 54.3 | 31.6 |
| Ethylene Selectivity (%) | 0 | 31.4 |
| $CO_2$ Selectivity (%) | 31.4 | 28.7 |
| CO Selectivity (%) | 14.3 | 3.0 |

As shown in Table 1, there was very little methane activation at 600° C. and no production of ethylene. At 650° C., methane conversion was higher, at 14.3%, and the ethylene selectivity was 31.4%.

For the oxidative methylation of toluene, four trials were conducted, at reaction temperatures between 550° C. and 650° C. All reaction conditions other than temperature were held constant during the four trials. The oxygen source was air. The methane to oxygen molar ratio was 5:1. The methane to toluene molar ratio was 15:1. The total flow of gasses was 500 cm$^3$/min (240 cm$^3$/min air, 244 cm$^3$/min methane, 0.076 cm$^3$/min liquid toluene), and the space velocity was 51,993 cm$^3$ g$^{-1}$ h$^{-1}$. Product samples were taken after twenty minutes of run time and analyzed for product distribution. The results of the trials are shown in the table below.

TABLE 2

Results for OMT over Ba/MgO catalyst

| | Reaction Temperature | | | |
|---|---|---|---|---|
| | 550° C. | 570° C. | 600° C. | 650° C. |
| Toluene Conversion (mol %) | 3.2 | 6.8 | 7.3 | 9.9 |
| Benzene Selectivity (%) | 65.8 | 85.4 | 74.5 | 49.3 |
| Ethylbenzene Selectivity (%) | 3.6 | 5.0 | 5.8 | 7.0 |
| Total Xylene Selectivity (%) | 2.9 | 2.0 | 2.2 | 2.5 |
| Styrene Selectivity (%) | 9.6 | 18.5 | 25.5 | 41.4 |
| Benzaldehyde Selectivity (%) | 29.5 | 1.2 | 0.6 | 0.3 |
| Total Stilbene Selectivity (%) | 0.2 | 0.3 | 0.4 | 0.3 |

The results are also shown in FIG. 1. FIG. 1 is a graphical representation of the data presented in Table 2. The x-axis shows temperature from 540° C. to 650° C. The y-axis on the left side of the graph corresponds to percent conversion of toluene. As can be seen, toluene conversion increased from 3% to 10% as temperature increased. The y-axis on the right side of the graph corresponds to percent selectivity for all of the products of the reactions. The products included benzene, ethylbenzene, xylene, styrene, benzaldehyde, and stilbene. Benzene was the product with the highest selectivity. However, its selectivity peaked at 570° C. and steadily decreased thereafter. Styrene, on the other hand, steadily increased with temperature. Because conversion and the selectivity of key products can vary with temperature, it may be possible to adjust product selectivity based on temperature. Benzene and styrene, for instance, can both be valuable products. The demands for these products may vary, and it can thus be useful to be able to control which of the two is the predominant product of OMT by adjusting the temperature. Selectivity of the other products was less variable. For benzaldehyde, the selectivity rapidly decreased from 30% to less than 1% at 575° C. Ethylbenzene selectivity, the total xylenes selectivity, and the stilbene selectivity remained low in all the trial runs.

COMPARATIVE EXAMPLE B

An oxidative catalyst was prepared comprising an oxide substrate, MgO, that was promoted with Li. The Li/MgO catalyst was used in the oxidative methylation of toluene. The catalyst included 2.5% Li by weight and was prepared from Lithium carbonate (13.69 g) salt (Sigma Aldrich, 98.0%) and MgO (16.304 g) (Fisher, 99%) by incipient wetness impregnation methodology in aqueous solution. The mixture was dried at 120° C. for 3 hours and then calcined at 850° C. in air for 1 hour. The catalyst was ground and sieved to 20-40 mesh size and 0.542 g of catalyst was loaded in a quartz reactor using quartz wool plugs and quartz chips to hold the catalyst bed in place. As a form of catalyst pretreatment, the reactor was heated to 850° C. under 100 ml/min of air and held for 2 hours. The reactor was then cooled down to 600° C. under helium to prepare for the OMT experiments.

For the oxidative methylation of toluene, the reaction temperature was 650° C., the oxygen source was air, the total flow of gasses was 335 cm$^3$/min (150 cm$^3$/min air, 150 cm$^3$/min methane, 0.167 cm$^3$/min liquid toluene), the methane to oxygen molar ratio was 5:1, and the methane to toluene ratio was 15:1. The reaction was performed twice, at two different space velocities. For the first trial, the space velocity was 37,085 cm$^3$ g$^{-1}$ h$^{-1}$. For the second trial, the space velocity was adjusted to 70,295 cm$^3$ g$^{-1}$ h$^{-1}$ by diluting the feed with nitrogen gas (150 cm$^3$/min air, 150 cm$^3$/min methane, 0.167 cm$^3$/min liquid toluene, 300 cm$^3$/min nitrogen). Space velocity is inversely related to residence time in the reactor, and modulation of space velocity influences the contact time between reactants and catalyst. At a higher space velocity, residence time and contact time are lower, and more reactants pass over the catalyst in a given period.

The results of the two OMT trials are shown in the table below. Gas and liquid samples were analyzed for product distribution at twenty minutes.

TABLE 3

Results for OMT over Li/MgO catalyst

| Space Velocity (cm$^3$g$^{-1}$h$^{-1}$) | 37,085 | 70,295 |
|---|---|---|
| Methane Conversion (mol %) | 1.3 | — |
| Acetylene Selectivity (%) | 0.000 | 0.000 |
| $CO_2$ Selectivity (%) | 18.0 | 13.0 |
| Ethane Selectivity (%) | 0.0 | 0.3 |
| Ethylene Selectivity (%) | 0.0 | 0.0 |
| CO Selectivity (%) | 5.6 | 3.8 |
| Toluene Conversion (mol %) | 4.3 | 3.7 |
| Benzene Selectivity (%) | 58.6 | 58.3 |
| Ethylbenzene Selectivity (%) | 2.6 | 2.3 |
| Styrene Selectivity (%) | 9.9 | 10.4 |
| $C_8$ Selectivity (%) | 15.0 | 16.0 |
| Stilbene Selectivity (%) | 2.6 | 8.1 |

At the higher space velocity, there was greater selectivity to styrene (10.4% as compared to 9.9%). For toluene, the conversion dropped from 4.3% to 3.7%. The selectivity to benzene and ethylbenzene formation did not change with increasing space velocity. However, stilbene selectivity increased dramatically from 2.6 to 8.1 mol %.

EXAMPLE C

An oxidative catalyst was prepared comprising a MgO substrate that was promoted with Na, Cs, and Re. The Na/Cs/Re/MgO catalyst was used in the oxidative coupling of methane and the oxidative methylation of toluene. The catalyst included 5% Na by weight (3.811 g) of sodium chloride, 5% Cs by weight (2.199 g) of cesium nitrate, and 0.01% Re by weight (0.5856 g) of rhenium chloride and MgO (23.4033 g) (Fisher, 99%) by incipient wetness impregnation methodology in aqueous solution. The mixture was dried at 120° C. for 3 h and then calcined at 850° C. in air for 1 h. The catalyst was ground and sieved to 20-40 mesh size (420-841 μm) and 0.597 g of catalyst was loaded into a quartz reactor using quartz wool plugs and quartz chips to hold the catalyst bed in place. For catalyst pretreatment, the reactor was heated to 850° C. under 100 ml/min of air and held for 2 hours. The reactor was then cooled down to 600° C. under helium to prepare for the OCM and OMT experiments.

Four OCM trials were conducted, at reaction temperatures between 600° C. and 750° C. In all trials, the oxygen source was air, the total flow of gasses was 500 cm$^3$/min (250 cm$^3$/min air, 250 cm$^3$/min methane), the methane to oxygen molar ratio was 5:1, and the space velocity was 50,251 cm$^3$ g$^{-1}$ h$^{-1}$. Product samples were taken after the twenty-five minutes of run time and analyzed for product distribution. The results of the trials are shown in the table below.

TABLE 4

Results for OCM over Na/Cs/Re/MgO catalyst

| | Temperature | | | |
|---|---|---|---|---|
| | 600° C. | 650° C. | 700° C. | 750° C. |
| Methane Conversion (wt %) | 0.2 | 0.4 | 1.0 | 4.8 |
| C$_2$ Selectivity (wt %) | 0.0 | 0.0 | 0.0 | 4.8 |
| Acetylene Selectivity (wt %) | 0.0 | 0.0 | 0.0 | 0.0 |
| Ethane Selectivity (wt %) | 0.0 | 0.0 | 0.0 | 3.8 |
| Ethylene Selectivity (wt %) | 0.0 | 0.0 | 0.0 | 1.0 |
| CO$_2$ Selectivity (wt %) | 0.0 | 17.6 | 14.6 | 9.8 |
| CO Selectivity (wt %) | 0.0 | 0.0 | 0.0 | 10.8 |

Five OMT trials were conducted, at reaction temperatures between 550° C. and 750° C. In all trials, the oxygen source was air, the total flow of gasses was 500 cm$^3$/min (244 cm$^3$/min methane, 240 cm$^3$/min air, 0.076 cm$^3$/min liquid toluene), the methane to oxygen molar ratio was 5:1, the methane to toluene molar ratio was 15:1, and the space velocity was 50,251 cm$^3$ g$^{-1}$ h$^{-1}$. Product samples were taken after the first twenty minutes of run time and analyzed for product distribution. The results of the trials are shown in the table below.

TABLE 5

Results for OMT over Na/Cs/Re/MgO

| | Temperature | | | | |
|---|---|---|---|---|---|
| | 550° C. | 600° C. | 650° C. | 700° C. | 750° C. |
| Toluene Conversion (%) | 1.7 | 1.9 | 3.3 | 12.1 | 39.9 |
| Benzene Selectivity (%) | 56.1 | 74.1 | 57.9 | 33.3 | 25.1 |
| Total Xylene Selectivity (%) | 3.6 | 3.3 | 3.4 | 2.9 | 1.9 |
| Stilbene Selectivity (%) | 3.3 | 0.9 | 0.5 | 0.2 | 0.2 |
| Benzaldehyde Selectivity (%) | 30.6 | 12.6 | 6.3 | 2.0 | 2.0 |
| Ethylbenzene Selectivity (%) | 3.7 | 5.0 | 8.4 | 8.6 | 4.5 |
| Styrene Selectivity (%) | 11.6 | 16.7 | 29.0 | 46.2 | 49.4 |

Figure 2:
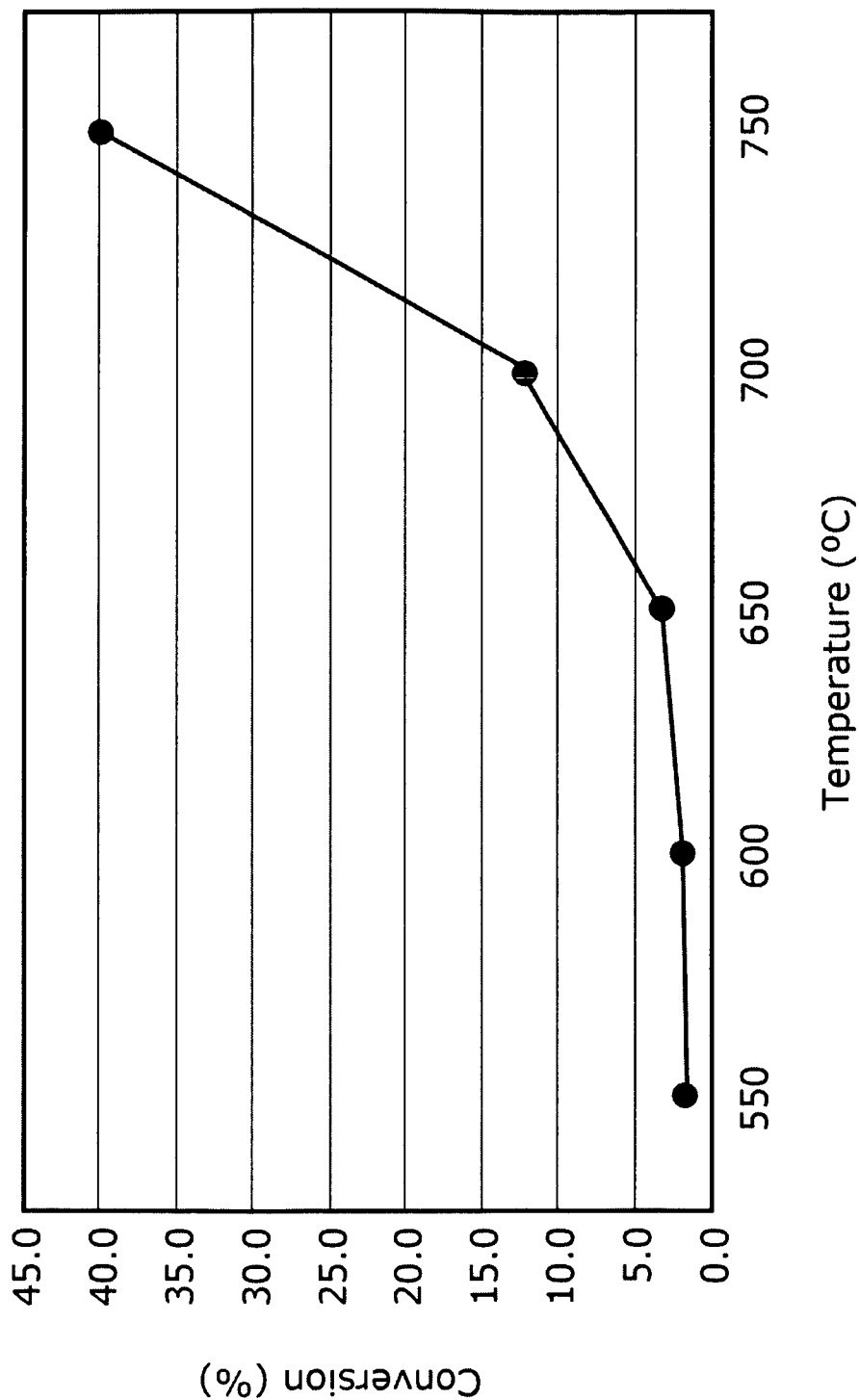
FIG. 2 is a chart showing the conversion of toluene over various temperatures, from the OMT trials conducted in Example C.
Figure 3:
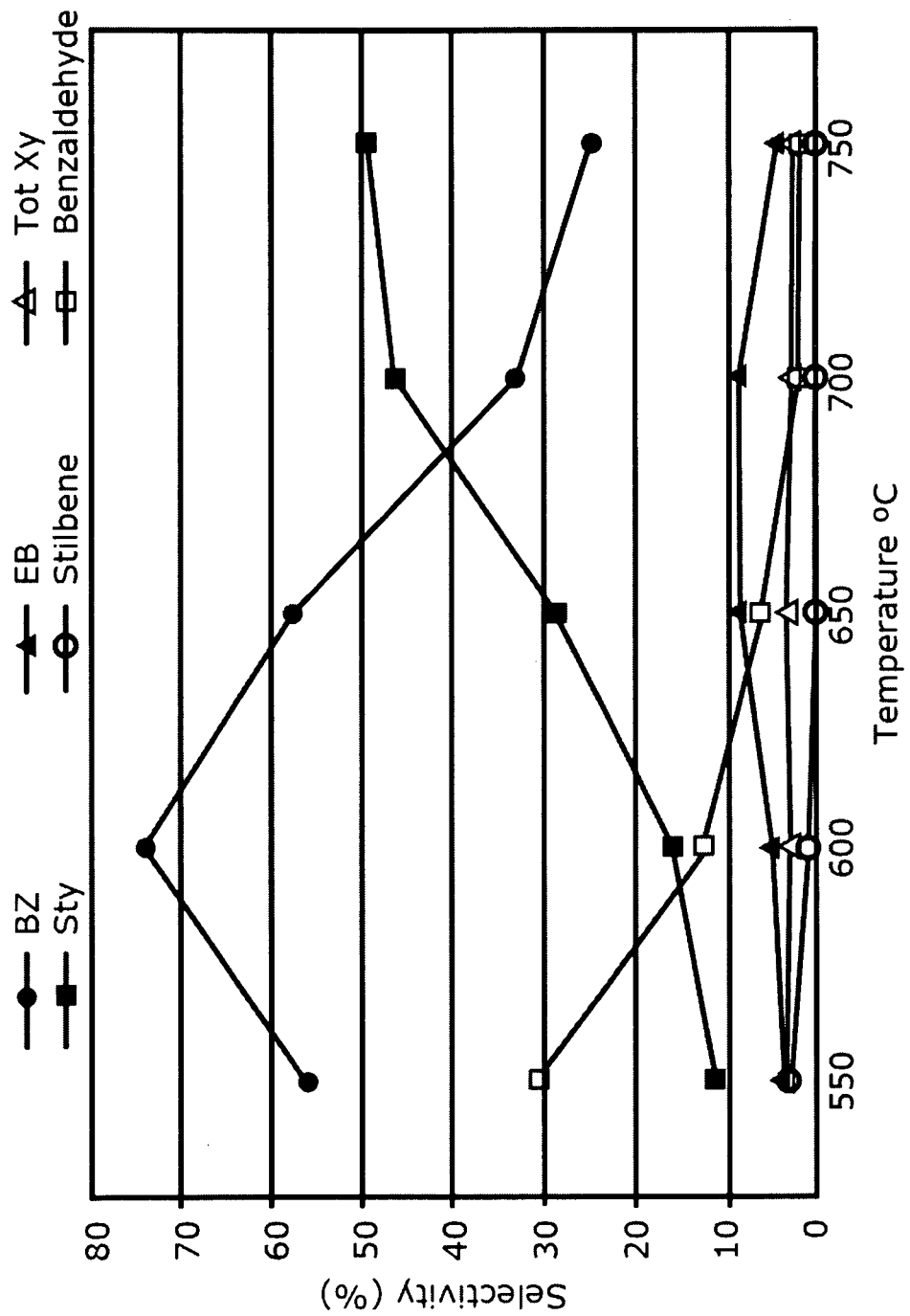
FIG. 3 is a chart showing the selectivity of various products obtained from the OMT trials conducted in Example C.

FIGS. 2 and 3 are graphical representations of the data shown in Table 5. FIG. 2 shows the data for toluene conversion, with temperature on the x-axis and percent conversion on the y-axis. The conversion of toluene increased from 1.7% at 550° C. to 39.9% at 750° C. FIG. 3 shows the data for selectivity. At temperatures from 550° C. to about 685° C., benzene is the predominant product, with selectivity above 50%. At around 685° C., the selectivity for benzene and that of styrene intersect and above 685° C., styrene is the predominant product. This approximate temperature of 685° C. also marks a transition in the rate of formation of styrene. The selectivity of styrene rises significantly from 550° C. to 685° C. (from 11.6% to 46.2%) and rises relatively little (from 46.2% to 49.4%) above 685° C.

The selectivity of the other products decreased or remained low over the temperatures explored. For instance, benzaldehyde selectivity decreased from 30.6% at 550° C. to 2.0% at 750° C.

Styrene is most commonly the desired product of OMT. However, depending on demand and process needs, other products can also be desired. Ethylbenzene, for instance, can be a desired product as the technology is well established for its conversion to styrene via dehydrogenation. It is thus a useful feature of this process that product distribution can be affected by modulation of reaction conditions such as temperature. Benzene was the product with the highest selectivity. However, its selectivity peaked at 600° C. and steadily decreased thereafter. Styrene, on the other hand, steadily increased with temperature. Because conversion and the selectivity of key products can vary with temperature, it may be possible to adjust product selectivity based on temperature. Benzene and styrene, for instance, can both be valuable products. The demands for these products may vary, and it can thus be useful to be able to control which of the two is the predominant product of OMT by adjusting the temperature.

EXAMPLE D

An oxidative catalyst was prepared comprising an oxide substrate, MgO, that was promoted with Ca and La. The Ca/La/MgO catalyst was used in the oxidative coupling of methane to toluene. The catalyst included 5% Ca by weight from Calcium oxide (2.10 g) and 5% La by weight from lanthanum oxide (3.51 g) and was prepared from calcium oxide salt, La$_2$O$_3$ (Sigma Aldrich, 98.0%) and MgO (24.38 g) (Fisher, 99%) by incipient wetness impregnation methodology in aqueous solution. The mixture was dried at 120° C. for 3 hours and then calcined at 850° C. in air for 1 hour. The catalyst was ground and sieved to 20-40 mesh size and 0.661 g of catalyst was loaded in a quartz reactor using quartz wool plugs and quartz chips to hold the catalyst bed in place. As a form of catalyst pretreatment, the reactor was heated to 850° C. under 100 ml/min of air and held for 2 hours. The reactor was then cooled down to 600° C. under helium to prepare for the OMT experiments.

Four OMT trials were conducted over the Ca/La/MgO catalyst at temperatures of from 550° C. to 700° C. Reactions conditions other than temperature were held constant. The oxygen source was air. The total flow of gasses was 498 cm$^3$/min (244 cm$^3$/min methane, 240 cm$^3$/min air, 0.067 cm$^3$/min liquid toluene). The methane to oxygen molar ratio was 5:1. The methane to toluene molar ratio was 15:1. The space velocity was 45,204 cm$^3$ g$^{-1}$ h$^{-1}$. The products were analyzed after twenty minutes for product distribution. The table below shows results for the four OMT trials.

TABLE 6

Results of OMT over Ca/La/MgO

| | Temperature | | | |
|---|---|---|---|---|
| | 550° C. | 600° C. | 650° C. | 750° C. |
| Toluene Conversion (%) | 3.0 | 5.8 | 7.5 | 12.6 |
| Benzene Selectivity (mol %) | 60.6 | 40.4 | 39.5 | 28.1 |
| Total Xylene Selectivity (mol %) | 5.0 | 4.6 | 4.1 | 3.5 |
| Stilbene Selectivity (mol %) | 0.3 | 0.2 | 0.4 | 0.0 |
| Benzaldehyde Selectivity (mol %) | 1.4 | 0.1 | 0.0 | 0.0 |
| Ethylbenzene Selectivity (mol %) | 5.9 | 5.7 | 5.2 | 4.5 |
| Styrene Selectivity (mol %) | 39.7 | 49.7 | 50.4 | 58.2 |

Figure 4:
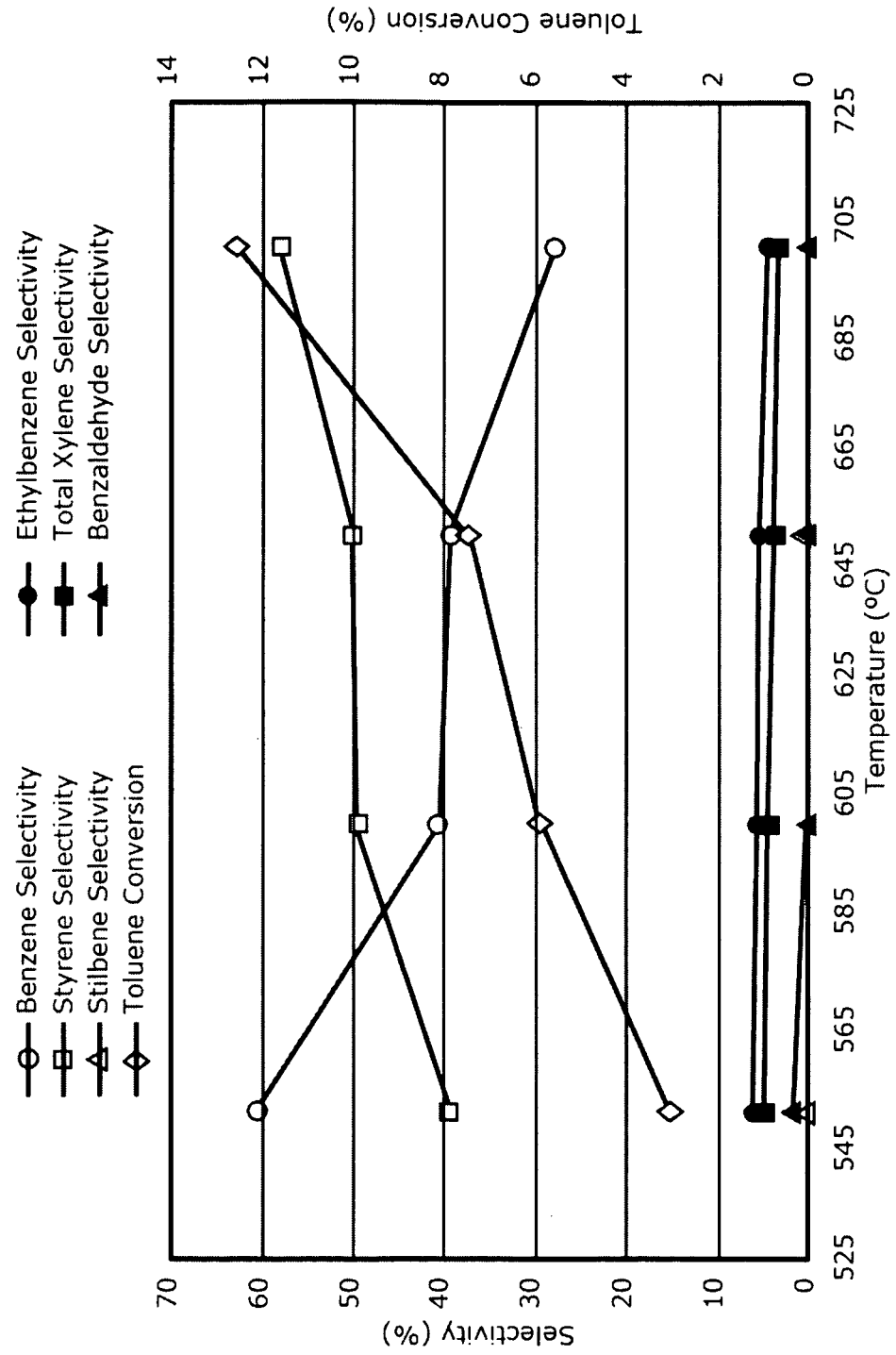
FIG. 4 is a chart showing data, including conversion and selectivity, of the OMT trials conducted in Example D.

FIG. 4 is a graphical representation of the data shown in Table 6. Toluene conversion increased with increasing temperature, going from about 3% conversion at 550° C. to nearly 13% conversion at 700° C. Product distribution also varied with temperature. Styrene increased in selectivity from about 40% at 550° C. to nearly 60% at 700° C. All other products had low selectivity and generally decreased in selectivity as the temperature rose.

EXAMPLE E

An oxidative catalyst was prepared comprising an oxide substrate, MgO, that was promoted with Sr and La. The Sr/La/MgO catalyst was used in the oxidative coupling of methane and the oxidative methylation of toluene. The catalyst included 5% Sr by weight from strontium nitrate (3.62 g) and 5% La by weight from lanthanum oxide (3.51 g) and was prepared from $Sr(NO_3)_2$ salt, $La_2O_3$ (Sigma Aldrich, 98.0%) and MgO (22.85 g) (Fisher, 99%) by incipient wetness impregnation methodology in aqueous solution. The mixture was dried at 120° C. for 3 hours and then calcined at 850° C. in air for 1 hour. The catalyst was ground and sieved to 20-40 mesh size and 0.855 g of catalyst was loaded in a quartz reactor using quartz wool plugs and quartz chips to hold the catalyst bed in place. As a form of catalyst pretreatment, the reactor was heated to 850° C. under 100 ml/min of air and held for 2 hours. The reactor was then cooled down to 600° C. under helium to prepare for the OCM and OMT experiments.

Five OCM trials were conducted using the Sr/La/MgO catalyst. The five trials correspond to five temperatures between 500° C. and 700° C. For all five trials, the oxygen source was air, the total flow of gasses was 500 $cm^3$/min (250 $cm^3$/min methane, 250 $cm^3$/min air), the methane to oxygen molar ratio was 5:1, and the space velocity was 35,088 $cm^3$ $g^{-1}$ $h^{-1}$. After the first 25 minutes, the corresponding gas samples were analyzed for product distribution and selectivity. Table 7 shows the results of the five OCM trials.

TABLE 7

Results for OCM over Sr/La/MgO catalyst

| | Temperature | | | | |
|---|---|---|---|---|---|
| | 500° C. | 550° C. | 600° C. | 650° C. | 700° C. |
| Methane Conversion (wt %) | 19.4 | 23.1 | 34.9 | 36.1 | 35.8 |
| $C_2$ selectivity (%) | 3.8 | 3.2 | 29.9 | 33.4 | 33.8 |
| Acetylene Selectivity (%) | 0 | 0 | 0.9 | 0.7 | 0.7 |
| Ethane Selectivity (%) | 3.8 | 3.2 | 14.2 | 16.1 | 15.6 |
| Ethylene Selectivity (%) | 0 | 0 | 14.8 | 16.6 | 17.5 |
| $CO_2$ Selectivity (%) | 0 | 1.5 | 5.7 | 3.9 | 3.0 |
| CO Selectivity (%) | 44.5 | 40.4 | 3.0 | 3.5 | 3.5 |

The selectivity of $C_2$ products (acetylene, ethane, and ethylene) was limited and the partial oxidation product, CO, took up a large portion of the products below 600° C. At 600° C. and above, methane conversion was higher, $C_2$ products had a higher selectivity while the selectivity for CO was lower.

Figure 5:
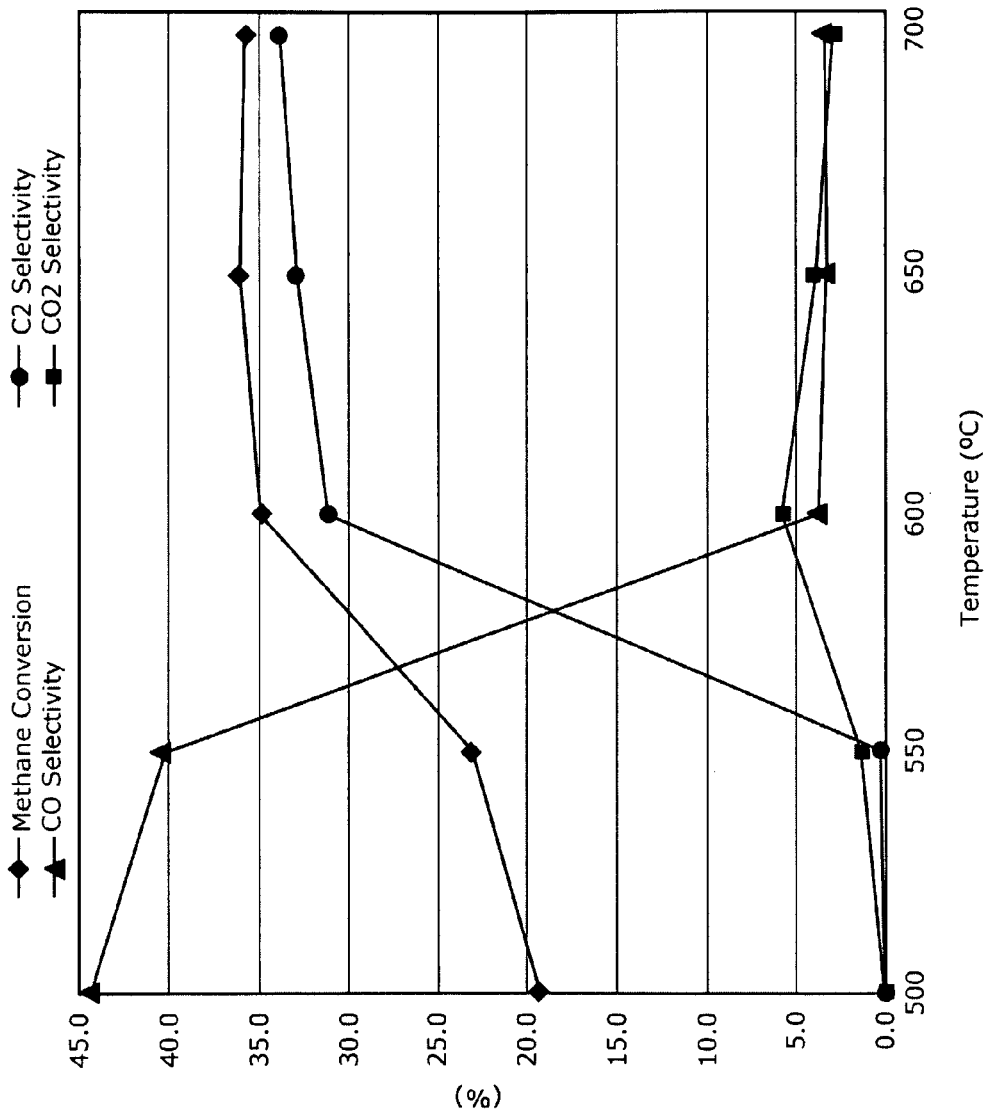
FIG. 5 is a chart showing data, including conversion and selectivity, of the OCM trials conducted in Example E.

FIG. 5 is a graphical representation of the data shown in Table 7. At a temperature between 550° C. and 600° C., methane conversion and $C_2$ selectivity rise suddenly, while CO selectivity drops dramatically. As in the previous example, these results indicate that temperature can be modulated to adjust product distribution.

The Sr/La/MgO catalyst was used in four trials of OMT at temperatures from 500° C. to 650° C. All reaction conditions other than temperature were held constant during these trials. The oxygen source was air. The total flow of gasses was 498 $cm^3$/min (244 $cm^3$/min methane, 240 $cm^3$/min air, 0.067 $cm^3$/min liquid toluene). The methane to oxygen molar ratio was 5:1. The methane to toluene molar ratio was 15:1. The space velocity was 34,947 $cm^3$ $g^{-1}$ $h^{-1}$. The products were sampled after 20 minutes and analyzed. The table below shows the results of the four OMT trials.

TABLE 8

Results of OMT over Sr/La/MgO catalyst

| | Temperature | | | |
|---|---|---|---|---|
| | 500° C. | 550° C. | 600° C. | 650° C. |
| Toluene Conversion (wt %) | 0.4 | 1.1 | 6.1 | 15.8 |
| Benzene Selectivity (wt %) | 30.4 | 51.0 | 40.4 | 16.2 |
| Total Xylene Selectivity (wt %) | 15.8 | 6.7 | 3.9 | 2.5 |
| Stilbene Selectivity (wt %) | 1.3 | 0.2 | 0.2 | 0.3 |
| Benzaldehyde Selectivity (wt %) | 21.2 | 5.7 | 0.1 | 0.0 |
| Ethylbenzene Selectivity (wt %) | 5.2 | 6.6 | 7.5 | 4.5 |
| Styrene Selectivity (wt %) | 4.5 | 22.2 | 43.0 | 42.1 |

Figure 6:
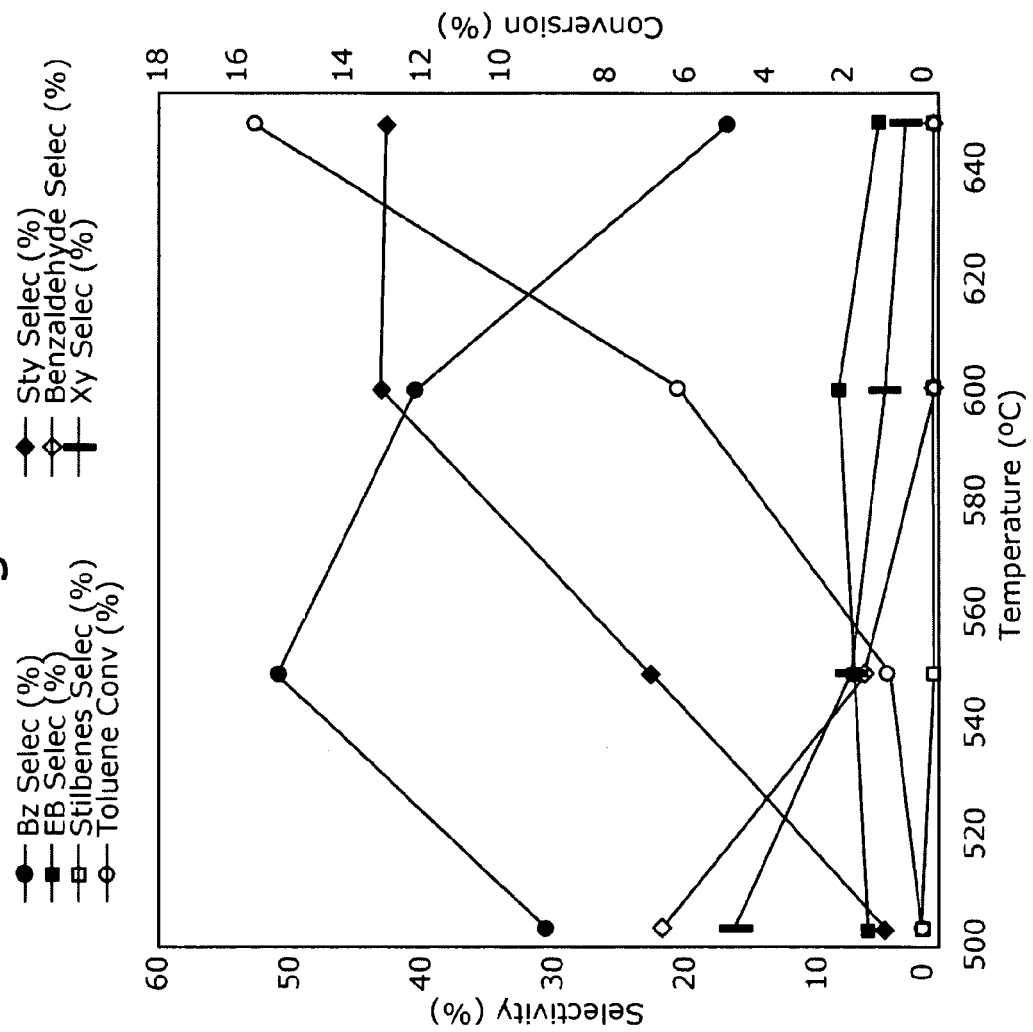
FIG. 6 is a chart showing data, including conversion and selectivity, of the OMT trials conducted in Example E.

FIG. 6 is a graphical representation of the data shown in Table 8. The toluene conversion increased with increasing temperature, from 0.4 wt % at 500° C. to 15.8 wt % at 650° C. Styrene selectivity also showed a general increase with increasing temperature, increasing from 4.5 wt % at 500° C. to 43.0 wt % at 600° C. The benzene selectivity showed an initial increase in selectivity, with a peak of 51 wt % at 550° C. At temperatures above 550° C., however, benzene selectivity decreased down to 16.2 wt % at 650° C. At about 595° C., the benzene and styrene selectivity intersect at about 42.0 wt %. This temperature also seems to mark a change in the rate of formation of styrene. Below 595° C., styrene selectivity increased steadily with increasing temperature, but above this temperature styrene selectivity changed very little. All the products except benzene and styrene showed a general decrease in selectivity with increasing temperature.

Figures are used herein to illustrate data, which are shown as data points on a graph. Lines connecting the data points are used to guide the eye and assist in illustrating general trends of the data. The lines are not intended as a predictor of where additional data points would necessarily fall, if they were available.

The term "$C_2$ selectivity" as used herein is the cumulative selectivity of acetylene, ethane, and ethylene.

The abbreviation of "OCM" as used herein refers to oxidative coupling of methane. For instance, methane can couple with methane to form higher hydrocarbons such as ethane or ethylene.

The abbreviation of "OMT" as used herein refers to the oxidative methylation of toluene to form new compounds. For instance, toluene can couple with methane to form ethylbenzene and/or styrene.

Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide substrate for narrower terms such as consisting of, consisting essentially of, comprised substantially of, etc.

As used herein the space velocity shall be defined as: space velocity=[feed flow as vapor ($cm^3$/h)]/[catalyst weight (g)].

The above examples demonstrate possible embodiments of the present invention. Depending on the context, all references herein to the "invention" may in some cases refer to certain specific embodiments only. In other cases it may refer to subject matter recited in one or more, but not necessarily all, of the claims. While the foregoing is directed to embodiments, versions and examples of the present invention, which are included to enable a person of ordinary skill in the art to make and use the inventions when the information in this patent is combined with available information and technology, the inventions are not limited to only these particular embodiments, versions and examples. Other and further embodiments, versions and examples of the invention may be devised without departing from the basic scope thereof and the scope thereof is determined by the claims that follow.

What is claimed is:

1. A catalyst for the oxidative coupling of hydrocarbons consisting essentially of:
   (A) Mg, wherein Mg is present in the catalyst in an amount ranging from 40 weight percent to 90 weight percent based on a total weight of the catalyst;
   (B) Na and Re, wherein Na and Re are each present in the catalyst in an amount ranging from 0.01 weight percent to 10 weight percent based on the total weight of the catalyst;
   (C) Cs, wherein Cs is present in the catalyst in an amount ranging from 0.01 weight percent to 10 weight percent based on the total weight of the catalyst; and
   (D) oxygen, wherein the Mg and the oxygen are present in the catalyst as MgO, wherein O is present in the catalyst in an amount ranging from 10 weight percent to 45 weight percent based on the total weight of the catalyst, and wherein at least 95 weight percent of the catalyst is made of (A), (B), (C), and (D).

2. The catalyst according to claim 1, wherein the catalyst is calcined after the elements are combined.

3. The catalyst according to claim 2, wherein the calcination comprises heating to above 750° C.

4. The catalyst according to claim 2, wherein the catalyst is capable of oxidative coupling of methane that takes place in a reactor at a temperature of from 600 to 750° C. exhibiting a methane conversion of from 0.2 to 4.8 weight percent.

5. The catalyst according to claim 2, wherein the catalyst is capable of oxidative coupling of methane that takes place in a reactor with a molar ratio of methane to oxygen of from 1:1 to 100:1.

6. The catalyst according to claim 1, wherein the catalyst is capable of oxidative coupling of hydrocarbons consisting of methane and toluene, and the products of the oxidative coupling of methane with toluene comprise ethylbenzene and styrene.

7. The catalyst according to claim 6, wherein the oxidative coupling of methane with toluene takes place in a reactor at a temperature of from 550 to 750° C. exhibiting a toluene conversion of from 1.7 to 39.9 weight percent.

8. The catalyst according to claim 6, wherein the oxidative coupling of methane with toluene takes place in a reactor with a molar ratio of methane to oxygen of from 1:1 to 100:1.

9. The catalyst according to claim 6, wherein the oxidative coupling of methane with toluene takes place in a reactor with a molar ratio of methane to toluene of from 1:1 to 50:1.

10. The catalyst according to claim 9, wherein the catalyst is pretreated to above 750° C. before it is used for the oxidative coupling of hydrocarbons.

11. The catalyst according to claim 1, wherein reaction products from the use of the catalyst can be adjusted by adjusting the temperature of the reaction.

12. The catalyst according to claim 1, wherein reaction products from the use of the catalyst can be adjusted by adjusting the space velocity of the reaction.

13. A catalyst for the oxidative coupling of hydrocarbons consisting essentially of:
   (A) Mg, wherein Mg is present in the catalyst in an amount ranging from 40 weight percent to 90 weight percent based on a total weight of the catalyst;
   (B) La, wherein La is present in the catalyst in an amount ranging from 0.01 weight percent to 10 weight percent based on the total weight of the catalyst;
   (C) Ca, wherein Ca is present in the catalyst in an amount ranging from 0.01 weight percent to 10 weight percent based on the total weight of the catalyst; and
   (D) oxygen, wherein the Mg and the oxygen are present in the catalyst as MgO, wherein O is present in the catalyst in an amount ranging from 10 weight percent to 45 weight percent based on the total weight of the catalyst, and wherein at least 95 weight percent of the catalyst is made of (A), (B), (C), and (D).

14. The catalyst of claim 13, wherein the catalyst is capable of oxidative coupling of hydrocarbons consisting of methane and toluene, and the products of the oxidative coupling of methane with toluene comprise ethylbenzene and styrene, wherein the oxidative coupling of methane with toluene takes place in a reactor at a temperature of from 550 to 750° C. exhibiting a toluene conversion of from 3.0 to 12.6 weight percent.

15. A catalyst for the oxidative coupling of hydrocarbons consisting essentially of:
   (A) Mg, wherein Mg is present in the catalyst in an amount ranging from 40 weight percent to 90 weight percent based on a total weight of the catalyst;
   (B) La, wherein La is present in the catalyst in an amount ranging from 0.01 weight percent to 10 weight percent based on the total weight of the catalyst;
   (C) Sr, wherein Sr is present in the catalyst in an amount ranging from 0.01 weight percent to 10 weight percent based on the total weight of the catalyst; and
   (D) oxygen, wherein the Mg and the oxygen are present in the catalyst as MgO, wherein O is present in the catalyst in an amount ranging from 10 weight percent to 45 weight percent based on the total weight of the catalyst, and wherein at least 95 weight percent of the catalyst is made of (A), (B), (C), and (D).

16. The catalyst of claim 15, wherein the catalyst is capable of oxidative coupling of hydrocarbons consisting of methane and toluene, and the products of the oxidative coupling of methane with toluene comprise ethylbenzene and styrene, wherein the oxidative coupling of methane with toluene takes place in a reactor at a temperature of from 500 to 650° C. exhibiting a toluene conversion of from 0.4 to 15.8 weight percent.

17. The catalyst according to claim 15, wherein the catalyst is capable of oxidative coupling of methane that takes place in a reactor at a temperature of from 500 to 700° C. exhibiting a methane conversion of from 19.4 to 35.8 weight percent.

18. A catalyst for the oxidative coupling of hydrocarbons consisting of at least 95 weight percent, based on a total weight of the catalyst, of:
   (A) Mg, wherein Mg is present in the catalyst in an amount ranging from 40 weight percent to 90 weight percent based on a total weight of the catalyst;
   (B) at least one element selected from the group consisting of Na, Re, and La wherein (B) is present in the catalyst in an amount ranging from 0.01 weight percent to 10 weight percent based on the total weight of the catalyst;
   (C) at least one element selected from the group consisting of Cs, Ca, and Sr, wherein (C) is present in the catalyst in an amount ranging from 0.01 weight percent to 10 weight percent based on the total weight of the catalyst; and
   (D) oxygen, wherein the Mg and the oxygen are present in the catalyst as MgO, wherein O is present in the catalyst in an amount ranging from 10 weight percent to 45 weight percent based on the total weight of the catalyst, and wherein at least 95 weight percent of the catalyst is made of (A), (B), (C), and (D).

* * * * *